United States Patent [19]

Ascher et al.

[11] Patent Number: 4,708,825
[45] Date of Patent: Nov. 24, 1987

[54] PROCESS FOR THE PRODUCTION OF PENICILLINS

[75] Inventors: Gerd Ascher, Wörgl; Kurt Riedl, Kufstein, both of Austria

[73] Assignee: Biochemie, Tyrol, Austria

[21] Appl. No.: 512,162

[22] Filed: Jul. 8, 1983

Related U.S. Application Data

[63] Continuation of Ser. No. 394,796, Jul. 2, 1982, abandoned, which is a continuation of Ser. No. 300,898, Sep. 9, 1981, abandoned, which is a continuation of Ser. No. 143,572, Apr. 25, 1980, abandoned.

[30] Foreign Application Priority Data

Apr. 25, 1979 [AT] Austria ................................ 3089/79
Sep. 4, 1979 [AT] Austria ................................ 5852/79
Sep. 4, 1979 [AT] Austria ................................ 5851/79

[51] Int. Cl.$^4$ .......................................... C07C 101/04
[52] U.S. Cl. ............................................... 2600/544 N
[58] Field of Search ........... 260/544 D, 544 N, 544 Y

[56] References Cited

U.S. PATENT DOCUMENTS 2,516,145 7/1950 Pritchard ............................ 548/227
3,925,418 12/1975 Williams et al. ................. 260/544 D

FOREIGN PATENT DOCUMENTS 500436 5/1930 Fed. Rep. of Germany ... 260/544 N
7810212 4/1979 Netherlands ................... 260/544 N

OTHER PUBLICATIONS

Finar, I. L., Organic Chemistry, vol. I (1963) Longmans, Publ. p. 374.

Primary Examiner—Paul J. Killos
Assistant Examiner—L. Hendriksen
Attorney, Agent, or Firm—Gerald D. Sharkin; Richard E. Vila

[57] ABSTRACT

The invention provides a novel method for producing phenylglycyl chloride hydrochlorides involving reaction of N-substituted phenylglycines with for example thionyl chloride and then gaseous hydrogen chloride, as well as certain novel starting materials for use in this process and certain end-products thereby produced.

7 Claims, No Drawings

PROCESS FOR THE PRODUCTION OF PENICILLINS

This is a continuation of application Ser. No. 394,796, filed July 2, 1982, now abandoned, which in turn is a continuation of application Ser. No. 300,898, filed Sept. 9, 1981, now abandoned, which in turn is a continuation of application Ser. No. 143,572, filed Apr. 25, 1980, now abandoned.

This invention relates to compounds of formula I,

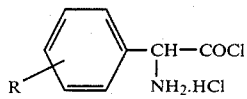

in which R is hydrogen or hydroxy, in particular 4-hydroxy.

The compounds of formula I possess an asymmetric carbon atom and may exist in racemic DL-form, or in isomeric D- or L-form. The invention is particularly concerned with the D-isomeric forms although it is not limited to these.

The compounds of formula I are known intermediates for the production of β-lactan antibiotics. They may for example be reacted with 6-aminopenicillianic acid (6-APA) of formula A,

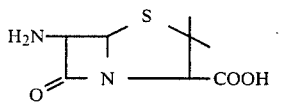

or a salt or protected form thereof, to yield valuable penicillins of formula B,

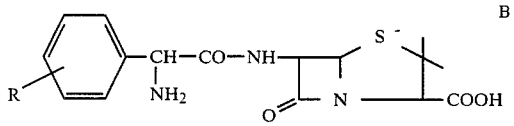

in which R is as defined above, or salts or protected forms (which may subsequently or in situ be disprotected) thereof. Their use in this manner is described in dozens of publications. The compounds in which R is hydrogen or 4-hydroxy in D-isomeric form, are of particular value since they can be connected in this manner to the well-known semisynthetic penicillins Ampicillin and Amoxycillin.

Likewise, they may be reached with 7-aminocephalosporanic acids or derivatives thereof of formula C,

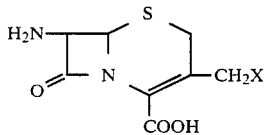

in which X is hydrogen, acetoxy or another group occurring in known cephalosporin antibiotics, e.g. —SZ, where Z is a heterocycle e.g. 1,2,3-triazol-5-yl or salts of protected forms thereof to yield valuable cephalosporins of formula D,

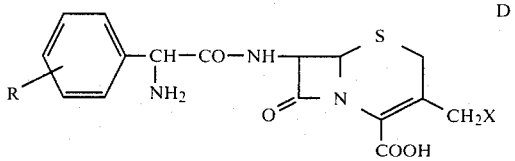

in which R and X are as defined above, or salts or protected forms (which may subsequently or in situ be disprotected) thereof. Their use in this manner is also described in many publications. Again the compounds of formula I in which R is hydrogen or 4-hydroxy in D-isomeric form are of particular value since they may be converted in this manner to, for example, the well-known semi-synthetic cephalosporin antibiotics Cephalexin (R=H, X=H), Cephaloglycin (R=H, X=acetoxy) or Cefatrizin (R=4—OH, X=1,2,3-triazol-5-yl).

The compounds of formula I, particularly those in which R is hydrogen, especially 4-hydroxy, present some difficulties in production. One generally applicable known process is described in Helv. Chim. Acta 39, 1525–1528 (1958) and proceeds according to the following reaction scheme:

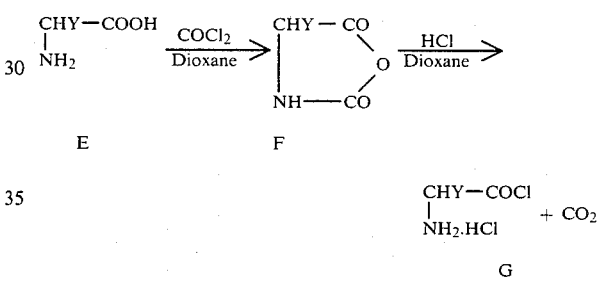

(Y being the residue of any aminoacid)

This process as applied to the production of D-(−)-4-hydroxyphenylglycyl chloride hydrochloride is described and claimed in W. German DOS No. 2,364,192, the process being carried out under anhydrous conditions, excess phosgene being removed from the reaction mixture after formation of the Leuck's anhydride F, and a large excess of gaseous hydrogen chloride being employed. The same process is described and claimed in W. German DOS No. 2,527,235 for the production of D-(−)-4-hydroxyphenylglycyl chloride hydrochloride dioxane hemisolvate.

This known process presents some disadvantages. Firstly, the difficulty of having to work with phosgene (which is highly toxic), secondly the need to remove excess phosgene from the reaction mixture after formation of the Leuck's anhydride F (since this is unstable in the presence of phosgene); thirdly, relatively strong conditions must be employed (preferably 60°–80° C. for formation of the intermediate F) and these tend to reduce the yield and purity of the final product.

The prior art also discloses in, for example, UK Pat. No. 1,241,844 a process for the production of D-(−)-4-hydroxyphenylglycyl chloride hydrochloride by reacting the free glycine with phosphorus pentachloride followed by gaseous hydrogen chloride. As explained in DOS No. 2,527,235, however, this process yields products having such poor physical characteristics that it cannot be used for large scale manufacture of penicillins and cephalosporins. Furthermore, the yields are very low.

The present invention seeks to overcome these disadvantages.

More particularly, the present invention provides a process for the production of compound of formula I, comprising reacting a compound of formula II,

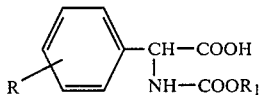

in which
R is as defined above, and
$R_1$ is straight-chain or branched lower alkyl, or benzyl with a sulphur- or phosphorus-containing acid chloride, and reacting the resulting product with gaseous hydrogen chloride.

When $R_1$ is lower alkyl, it preferably contains 1 to 6, particularly 1 to 4 carbon atoms. More preferably it is branched, particularly isopropyl.

The first step of the process of the invention is suitably carried out under anhydrous conditions, and in an inert organic solvent, such as a hydrocarbon, e.g. n-hexane, a chlorinated hydrocarbon, such as methylene chloride, an ester, or an ether, e.g. dioxane. Suitably, the step is carried out in the presence of a strong acid, such as trichloroacetic acid, trifluoroacetic acid, p-toluenesulphonic acid or methanesulphonic acid. The acid is conveniently present in amounts ranging from catalytic to equivalent amounts. Conveniently, the acid chloride is added to a mixture of the compound of formula II, the inert solvent and the strong acid at a temperature of about 0° C. The reaction mixture may then suitably be maintained at a temperature of from 30° C. to the reflux temperature of the mixture until reaction is complete. The reaction time typically varies from about 1 to 4 hours. The preferred acid chlorides for use in this step are S-containing acid chlorides, particularly thionyl chloride.

The resulting intermediate product can be isolated from the reaction mixture and purified in known manner. It may, however, alternatively be used as such without further purification in the second step of the process. In this step, the intermediate, or mixture containing the intermediate is suitably taken up in an inert solvent, preferably an ether, such as tetrahydrofuran, dioxane, or a dialkyl ether, e.g., diethylether, diisopropylether or di-n-butylether, anisole, tetrahydrofuran, or an aromatic hydrocarbon, such as toluene, an ester such as butylacetate, or a chlorinated hydrocarbon, such as methylene chloride.

Into this mixture, the gaseous hydrogen chloride is then suitably introduced. The step is conveniently carried out at a temperature of from 0° C. to room temperature. Preferably, the hydrogen chloride is introduced for an initial short period, until the mixture is saturated, at a relatively low temperature, for example −5° C. to 10° C. This may, if desired, then be followed by seeding the mixture with the desired product. Suitably, a weak stream of HCl gas is then introduced over a number of hours, e.g. for example up to 15 hours, at room temperature.

The resulting product may be isolated and purified in conventional manner. When the reaction mixure in the second step of the process contains dioxane as solvent or co-solvent, the product results in the formation of a dioxane hemi-solvate. When dioxane is not present, however, and the solvent comprises, for example, a dialkyl ether, tetrahydrofuran, anisole, an aromatic hydrocarbon, an ester or a chlorinated hydrocarbon, a solvate-free product results. The preferred solvents for production of the solvate-free product are dialkyl ethers, particularly diethyl-, diisopropyl- or di-n-butyl ether tetrahydrofuran, anisole, esters, preferably butyl acetate, and chlorinated hydrocarbons, e.g. methylene chloride, or mixtures thereof.

Relatively pure or crystalline, solvate-free D-(−)-4-hydroxyphenylglycyl chloride hydrochloride is believed in fact to be new since although this product is, on the face of it, described in W. German DOS No. 2,364,192, the procedures described specifically therein all operate with dioxane and the resulting product is believed in all cases to be the dioxane hemi-solvate. Other known products result in non-crystalline/impure products.

The process of the invention is both new and surprising, particularly as applied to the compounds of formula I in which R is hydroxy, more particularly 4-hydroxy, and more particularly to the compound D-(−)-4-hydroxyphenylglycyl chloride hydrochloride. It is stated in W. German DOS No. 2,364,192 that processes for the production of acid chloride hydrochloride of phenylglycine and substituted phenylglycines involving the use of thionyl chloride or phosphorus pentachloride are known but that these processes are unsatisfactory at least for hydroxy-substituted phenylglycines. The fact that the present process, employing e.g. thionyl chloride in a first step and HCl gas in the second step, results in good yields and purity of the end-products is therefore unexpected.

The present process also possesses clear advantages over the phosgene process discussed above in that the use of phosgene, a highly toxic material, is avoided and the need to remove the agent after the first step is also avoided.

The present process is all the more surprising since it has been found that phosgene and thionyl chloride are interchangeable in neither the prior art phosgene process, nor the present process. The prior art process does not function when phosgene is replaced by thionyl chloride, and the present process does not function when phosgene is employed in place of thionyl chloride.

In fact, the present process is believed to involve a different mechanism and sequence to that of the phosgene process. The precise nature of the intermediate involved in the present process has not been established but available data indicates that it is not the same as the Leuck's anhydride formed in the phosgene process, at least when applied to the production of compounds I in which R is hydroxy.

Certain of the compounds of formula II, employed as starting materials, in particular the compounds in which $R_1$ is isopropyl, are new. The compounds of formula II may for example be produced by reacting a salt of a compound of formula III,

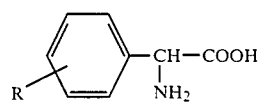

in which R is as defined above, with a compound of formula IV, $$X-CO-O-R_1 \quad\quad IV$$

in which
$R_1$ is as defined above, and
X is a leaving group, e.g. chlorine, bromine, iodine, azido or tosyl.

The process may be carried out in known manner, for example as described in the Examples hereinafter.

The following Examples, in which all temperatures are in degrees Centigrade illustrate the invention.

EXAMPLE 1

D-(−)-4-Hydroxyphenylglycyl chloride hydrochloride (Dioxane hemi-solvate)

25 g of D-(−)-N-isopropoxycarbonyl-4-hydroxyphenylglycine are suspended in 250 ml of methylene chloride and 16 g of trichloroaceticacid are added to the mixture. 16 ml of thionyl chloride are added with ice-cooling and stirring, and, after 10 minutes, the mixture is allowed to warm to room temperature and is stirred for 2 to 3 hours, at which starting material is no longer visible by TLC. After evaporation of the solvent, the residue is taken up in 300 ml of alkyl acetate and the solution is shaken once with 150 ml of water and then with 100 ml of brine. After drying with $Na_2SO_4$, the mixture is evaporated and the residue is taken up in 160 ml of dry dioxane and 80 ml of toluene. Gaseous HCl is introduced into the mixture, with ice-cooling, until saturation is reached. After seeding, and stirring at room temperature, crystallisation soon commences. After stirring overnight, the crystals of the heading compound are filtered off and identified by IR. Yield 28%.

EXAMPLE 2

D-(−)-Phenylglycyl chloride hydrochloride (Dioxane hemi-solvate)

2.5 g of D-(−)-N-isopropoxyphenylglycine, 25 ml of methylene chloride, 0.8 g of trichloroacetic acid and 1.2 ml of thionyl chloride are brought to reaction as described in Example 1. After 3 hours reaction time, the mixture is cooled, 5 ml of dioxane are added and HCl gas is introduced into the mixture until saturation is reached. After seeding, the mixture is stirred at room temperature for a number of hours and the product is then isolated. Yield 60%.

EXAMPLE 3

D-(−)-4-Hydroxyphenylglycyl chloride hydrochloride (Dioxane hemi-solvate)

2.5 g of D-(−)-N-isopropoxycarbonyl-4-hydroxyphenylglycine, 0.8 g of trichloroacetic acid and 25 ml of n-hexane are mixed, with ice-cooling, with 1.2 ml of thionyl chloride and the mixture is refluxed for 1 hour. The mixture is evaporated on a rotary evaporator and the residue is taken up in 16 ml of dioxane and 8 ml of toluene. After saturation which HCl gas, with cooling, seeding and stirring for several hours at room temperature, the product is filtered off, washed with dioxane/toluene (1:1), then with a little methylene chloride, and dried. The product is identified by IR and formation of the methyl ester (TLC). Yield 27%.

EXAMPLE 4

D-(−)-4-Hydroxyphenylglycyl chloride hydrochloride (Dioxane hemi-solvate)

12.5 g of D-(−)-N-isopropoxycarbonyl-4-hydroxyphenylglycine are suspended in 125 ml of methylene chloride, and 4 g of trichloroacetic acid and 8 ml of thionyl chloride are added. The mixture is heated under moderate reflux for 5 hours, with stirring and water exclusion, and is then cooled to 5°. 25 ml of dioxane are added and HCl gas is introduced for 30 minutes. After seeding, the mixture is stirred at room temperature n nuntil crystallisation commences. A weak stream of HCl gas is then bubbled through for 6 hours. The heading compound is filtered off on an inert gas-flushed filter, washed with a little methylene chloride and dried with $P_2O_5$. Yield 78%.

EXAMPLE 5

D-(−)-4-Hydroxyphenylglycyl chloride hydrochloride (Dioxane hemi-solvate)

2.25 g of D-(−)-N-methoxycarbonyl-4-hydroxyphenylglycine are dissolved in 20 ml of dioxane and 0.02 g of trichloroacetic acid are added. After dropwise addition of 0.8 ml of thionyl chloride in 5 ml of dioxane, the mixture is stirred, with moisture exclusion, for 4 hours at 50°. The mixture is then mixed with 8 ml of toluene, cooled to about 0° and HCl gas is introduced for 1 hour. The cooling means is removed and, after seeding, the mixture is stirred for several hours at room temperature. The precipitate is filtered off, washed with methylene chloride and dried. Yield 27%.

EXAMPLE 6

D-(−)-4-Hydroxyphenylglycyl chloride hydrochloride (Dioxane hemi-solvate)

2.25 g of D-(−)-N-methoxycarbonyl-4-hydroxyphenylglycine are suspended in 25 ml of methylene chloride, 0.8 ml of trichloroacetic acid are added, and 1.4 ml of thionylchloride are added at room temperature, dropwise, with stirring. The mixture is heated under moderate reflux, with moisture exclusion and stirring, for 4 to 5 hours. The mixture is cooled, mixed with 7 ml of dioxane, and hydrogen chloride gas is then introduced for 30 minutes. After seeding, the mixture is stirred at 20°-25° until crystallisation commences. A weak stream of HCl gas is then bubbled through for several hours and the product is filtered off with moisture exclusion, washed with methylene chloride and dried on a desiccator with $P_2O_5$ and silica gel. Yield 52%.

EXAMPLE 7

D-(−)-4-Hydroxyphenylglycyl chloride hydrochloride (Dioxane hemi-solvate)

2.4 g of D-(−)-N-ethoxycarbonyl-4-hydroxyphenylglycine are reacted and worked up as in Example 6, except that 1.6 g of trichloroacetic acid are employed instead of 0.8 g. Yield 30%.

EXAMPLE 8

D-(−)-4-Hydroxyphenylglycyl chloride hydrochloride (Dioxane hemi-solvate)

2.7 g of D-(−)-tert-.butoxycarbonyl-4-hydroxyphenylglycine are reacted as described in Example 6. Yield 70%.

EXAMPLE 9

D-(—)-4-Hydroxyphenylglycyl chloride hydrochloride
(Dioxane hemi-solvate)

3 g of D-α-benzyloxycarbonylamino-α-4-hydroxyphenylacetic acid are dissolved in 20 ml of dioxane, 0.05 g of trichloroacetic acid and 0.8 ml of thionyl chloride are added and the mixture is maintained for 1 hour at 50°, with moisture exclusion and magnetic stirring. After addition of 8 ml of toluene, the mixture is cooled to −5° and dry HCl gas is introduced for 1 hour. After seeding, the mixture is stirred for 4 hours at room temperature whereupon the heading compound separates out, is isolated and is dried in a vacuum desiccator over $P_2O_5$ and silica gel. Yield 56%.

EXAMPLE 10

D-(—)-4-Hydroxyphenylglycylchloride-hydrochloride 12.5 g of D-(—)-N-isopropoxycarbonyl-4-hydroxyphenylglycine in 125 ml of methylene chloride, are reacted with 8 g of trichloracetic acid and 8 ml of thionyl chloride at 40°, for a period of 3 hours. The mixture is cooled with ice water, 100 ml of diisopropyl ether are added and HCl gas is introduced to the mixture for 1½ hours. Stirring overnight at room temperature, yields a well crystallised, solvate-free product. Yield 80%.

EXAMPLE 11

D-(—)-4-Hydroxyphenylglycylchloride hydrochloride

The mixture resulting from reaction of thionylchloride with D-(—)-N-isopropoxycarbonyl-4-hydroxyphenyl glycine, as described in Example 10, is mixed with 100 ml of di-N-butylether and is converted to the heading compound by introduction of HCl gas. Yield 81%.

EXAMPLE 12

D-(—)-4-Hydroxyphenylglycylchloride-hydrochloride

In manner analogous to that described in Example 10, but employing in place of the 100 ml of diisopropyl ether, either 75 ml of anisol, 50 ml of tetrahydrofuran, or 75 ml of diethyl ether, the heading compound is obtained. Yield:
(a) Anisol: 47%
(b) Tetrahydrofuran: 72%
(c) Diethyl ether: 83%

EXAMPLE 13

D-(—)-4-Hydroxyphenylglycyl chloride hydrochloride

A mixture of 38 g of p-toluenesulphonic acid, 125 ml of methylene chloride and 15 ml of thionyl chloride is heated to reflux for 1-1½ hours. 50 g of D-(—)-N-isopropoxycarbonyl-4-hydroxyphenyl glycine and 30 ml of thionyl chloride are added and the mixture is heated to mild boiling for 2 hours. After addition of 200 ml of dry butylacetate, HCl gas is introduced with cooling. The mixture is then stirred for 1 hour at 5°, and the HCl introduction is repeated (30 minutes). After a further 30 minutes stirring at 15°, and addition of 400–500 ml of dry methylene chloride, the mixture is stirred for 15 hours at room temperature and the reaction product is filtered off on a glass frit filter with moisture exclusion. After washing with methylene chloride, the product is dried at room temperature on a vacuum desiccator. Yield 85%.

EXAMPLE 14

D-(—)-4-Hydroxyphenylglycyl chloride hydrochloride
(Dioxane hemi-solvate)

190 g of p-Toluenesulphonic acid/water in 625 ml of methylene dichloride are stirred for a short time with 119 g of thionyl chloride. 253 g of D-(—)-N-isopropoxycarbonyl-4-hydroxyphenyl glycine and 238 g of thionyl chloride are added, and the mixture is refluxed for 2½ to 3 hours whereupon after a short time a clear solution results. The mixture is cooled to 0° and, after addition of 500 ml of dioxane, about 170 g of HCl gas are introduced with external cooling until the content of HCl is 100 mg/ml. The mixture is finally stirred for 10 hours at room temperature and the precipitated product is filtered off, washed with dioxane/methylene chloride (1:1) and methylene chloride, and dried for 24 hours in vacuo.

Yield 86%.

The following Examples illustrate the production of starting materials of formula II.

(a)

D-(—)-N-Isopropoxycarbonyl-4-hydroxyphenylglycine 1. 40 g of D-(—)-4-Hydroxyphenylglycine are suspended in 320 ml of water and mixed with a solution of 9.6 g of sodium hydroxide in 80 ml of water at room temperature. A clear solution with a pH value of 9.7 results. Two further solutions are simultaneously prepared—9.9 g of sodium hydroxide in 80 ml of water and 29.2 ml of isopropylchloroformate in 50 ml of acetone—and are added dropwise so that the pH remains between 9.5 and 9.7 and the temperature does not rise above 25°. The mixture is stirred for 2 hours at room temperature. End pH 9.6. The acetone is evaporated off and the aqueous solution is extracted once with 50 ml of ether and is acidified with hydrochloric acid (1:1) and the acylation product is extracted 3 times with in total 250 ml of ethyl acetate. The purified extracts are dried and the ethyl acetate is evaporated off as far as possible. The residue is taken up in chloroform, dissolved by heating, and the mixture ie evaporated to remove the ethyl acetate as far as possible. The residue is taken up in 150 ml of chloroform, again heated, and the crystallisation is completed by addition of 60 ml of hexane. The product shows a m.p. of 163°–164° after drying.

2. The process of Example a1 above is repeated up until evaporation of the acetone. The resulting solution is filtered, mixed with 40 ml of concentrated ammonia or the corresponding amount of sodium hydroxide, and allowed to stand for 1 to 2 hours at room temperature. The mixture is then acidified with hydrochloric acid (1:1) with cooling and slow stirring, to a pH of 1.5 to 2 and on appearance of turbidity is seeded. Stirring is continued until crystallisation is complete. The product is identified by titration and IR.

3. 500 g of D-(—)-4-Hydroxyphenylglycine are suspended in 4 liters of water, the suspension is cooled to 2° to 5°, and a solution of 360 g of sodium hydroxide in 1 liter of water is added slowly, dropwise. The temperature is maintained at or below 5°. 900 ml of isopropylchloroformate are then added. The temperature of 5° again being maintained. The mixture is stirred for 1 hour with ice cooling, and then 780 ml of 10N NaOH are added. After 30 minutes at 20°, the mixture is filtered, the filtrate is acidified with sulphuric acid until it becomes turbid. After 5-10 minutes crystallisation time, further sulphuric acid is added with stirring until a pH of 2.0 is reached. To complete the crystallisation, the mixture is stirred for 15-30 minutes with ice cooling. The mixture is washed with water and in a vacuum drying cupboard first at 50°, then at 80°-90°, dried. The thus obtained heading compound is pure according to TLC, shows a melting point of 162°-164° and has a specific rotation of $[\alpha]_D^{20} = -155°$ (c=1 in methanol).

(b)
D-(−)-N-Methoxycarbonyl-4-hydroxyphenylglycine 40 g of D-(−)-4-hydroxyphenylglycine in 320 ml of water are mixed with a solution of 9.6 g of NaOH in 80 ml of water. To this is added a mixture of 9.6 g of NaOH in 80 ml of water and 19.8 ml of methylchloroformate in 40 ml of acetone, with water cooling, dropwise, so that a pH of 9.5 to 9.8 is maintained. 35 ml of 3N NaOH are additionally required. After stirring for 2 hours at room temperature the end pH is 9.5. The acetone is evaporated off, the mixture is filtered, and the aqueous phase is acidified with hydrochloric acid (1:1), and extracted with ethyl acetate. The mixture is evaporated and the residue is recrytallised from chloroform/hexane to obtain the pure heading compound. M.pt. 134°-137°.

D-(−)-N-Isopropoxycarbonyl-phenylglycine 113.1 g of D-(−)-phenylglycine are suspended in 1 liter of water and the pH is adjusted to 10.2 to 10.4 by addition of 50% NaOH with cooling (ice water) and stirring. 225 ml of Isopropylchloroformate and 50% sodium hydroxide are simultaneously added so that the mentioned pH is maintained. The reaction mixture is then basified to pH 12-13 and stirred at this pH for 40 minutes. The practically clear solution is acidified with concentrated hydrochloric acid with cooling until it becomes turbid. The mixture is seeded to commence crystallisation and after 20 minutes the pH is further depressed to 2.0. After a crystallisation time of 30 minutes the mixture is filtered and the residue washed 5 times with 100 ml of water and dried in a vacuum drying cupboard over silica gel at 50°-60°. After rubbing it is then dried for a further 16-17 hours at 60°-70°. M.p. 116°-120° (from ethyl acetate).

The further compounds of formula II employed in the foregoing Examples may be obtained in manner analogous to that described in Examples (a) to (c) above.

Characterisation of D-(−)-4-hydroxyphenylglycyl chloride hydrochloride (dioxane hemi-solvate):

$[\alpha]_{20}^D = -95°$ (c=1; 1 NHCl)

Solvent content (gc)=Dioxane 16%; $CH_2Cl_2$ 0.2%.
(IR peaks cm$^{-1}$: 3280(s); 1770(s); 1735(s), 1210(s); 1170(s); 865(s).

Characterisation of solvate-free crystalline D-(−)-hydroxyphenylglycylchloride-hydrochloride:

$[\alpha]_{20}^D = -112$ (c=1; 1 NHCl)

Solvent content (gc)=Butyl acetate 0.5%; $CH_2Cl_2$ 0.2%.
IR peaks cm$^{-1}$=3000(Br); 1735(s); 1170(s); 830.
M.pt. not determinable because of decomposition.

What we claim is:

1. A process for the production of a compound of formula I,

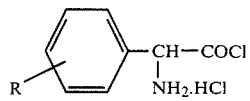

in which R is hydroxy, comprising reacting a compound of formula II,

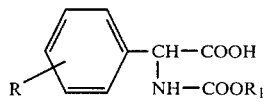

in which
R is as defined above, and
$R_1$ is straight-chain or branched lower alkyl, or benzyl
with thionyl chloride in the presence of a strong acid, and reacting the resulting product with gaseous hydrogen chloride.

2. A process according to claim 1, in which the strong acid is trichloroacetic acid, trifluoroacetic acid, p-toluenesulphonic acid or methane sulphonic acid.

3. A process according to claim 1 in which the reaction with gaseous hydrogen-chloride is carried out in an inert dioxane-containing solvate to obtain the product in the form of a dioxane hemi-solvate.

4. A process according to claim 3, for the production of D-(−)-4-hydroxyphenylglycyl chloride hydrochloride dioxane hemi-solvate.

5. A process according to claim 1 in which the reaction with gaseous hydrogen chloride is carried out in an inert solvent not containing dioxane, to obtain the product in solvate-free form.

6. A process according to claim 5, in which the inert solvent comprises a dialkyl ether, tetrahydrofuran, anisole, an aromatic hydrocarbon, an ester or chlorinated hydrocarbon.

7. A process according to claim 5 for the production of solvate-free D-(−)-4-hydroxyphenylglycyl chloride hydrochloride.

* * * * *